United States Patent [19]

Abdulhay

[11] Patent Number: 4,757,826
[45] Date of Patent: Jul. 19, 1988

[54] ENDOCERVICAL BIOPSY INSTRUMENT

[76] Inventor: Gazi Abdulhay, 4268 Albert Cir., Lake Oswego, Oreg. 97034

[21] Appl. No.: 933,231

[22] Filed: Nov. 20, 1986

Related U.S. Application Data

[63] Continuation-in-part of Ser. No. 729,268, May 1, 1985, abandoned.

[51] Int. Cl.$^4$ ............................................. A61B 10/00
[52] U.S. Cl. ..................................... 128/757; 128/304
[58] Field of Search ................ 128/757, 749, 756, 304

[56] References Cited

U.S. PATENT DOCUMENTS

| | | | |
|---|---|---|---|
| 2,437,329 | 3/1948 | Moore | 128/757 |
| 2,471,088 | 5/1949 | Anre | 128/757 |
| 2,495,794 | 1/1950 | Weller | 128/757 |
| 3,412,733 | 11/1968 | Ross | 128/305 |
| 3,485,236 | 12/1969 | Frost | 128/757 |
| 3,945,372 | 3/1976 | Milan | 128/757 |
| 4,054,127 | 10/1977 | Milan | 128/757 |
| 4,441,509 | 4/1984 | Kotsifas et al. | 128/757 |

*Primary Examiner*—Kyle L. Howell
*Assistant Examiner*—John C. Hanley
*Attorney, Agent, or Firm*—Klarquist, Sparkman, Campbell, Leigh & Whinston

[57] ABSTRACT

A biopsy instrument for the collection and extraction of endocervical tissue samples is disclosed. The instrument has a sample extraction head preferably ellipsoid or cylindrical in shape and of one-piece construction. The head contains one or more longitudinal blade portions integral with the surface of the head. Directly adjacent to each blade portion is a sample collection well. The well is of sufficient depth to permit the retention and removal of tissue specimens.

2 Claims, 2 Drawing Sheets

ENDOCERVICAL BIOPSY INSTRUMENT

BACKGROUND OF THE INVENTION

This application is a continuation-in-part of application Ser. No. 729,268 now abandoned, filed May 1, 1985.

The present invention relates to biopsy instruments, and more particularly to biopsy instruments for extracting endocervical tissue specimens.

In diagnosing cervical cancer, endocervical tissue biopsies are required. The term "endocervical" pertains to the inner canal of the cervix directly ahead of the endometrial cavity. To avoid delays and physical discomfort to the patient, the tissue samples must be removed as accurately and quickly as possible. Otherwise, repeated samplings may be required. Repeated samplings are undesirable from a physical, emotional, and economic standpoint.

Numerous devices have been created to extract tissue samples from the endocervical canal. U.S. Pat. No. 3,013,553 to Averbach describes an instrument known as a "trachelotome". The Averbach instrument uses an elongate cutting head having a removable, straight-edged blade. U.S. Pat. Nos. 2,827,039 and 2,898,906 to Seiger describe biopsy instruments having a removable, angled knife blade mounted directly above a rounded guide member. The rounded guide member has a blunt end. The guide member facilitates placement of the blade within the cervix. U.S. Pat. Nos. 3,633,565 and 3,774,590 to McDonald describe a cervical biopsy instrument having a flat, wedge-shaped cutting head. Cutting blades are located on each side of the head, each blade having an adjoining groove for collection of tissue samples. The cutting head also comprises two wing-shaped portions projecting outwardly from each side of the head. Their function is to collect specimens from the outer, exocervical regions of the cervix.

In contrast to the above instruments, all of which comprise substantially flat cutting heads, other instruments are tubular in design. These cutters require rotational motion for sample extraction. For example, U.S. Pat. No. 2,729,210 to Spencer describes a biopsy instrument having a hollow, frusto-conical cutting head with a removable blade and detachable blade clamp. To extract a tissue sample, the head is rotated and the sample is collected on the inside of the hollow head. Disassembly of the cutting head permits access to and removal of the collected tissue samples. U.S. Pat. No. 2,749,909 to Ullery et al. describes a similar instrument. The Ullery instrument uses a hollow, conical head having a frontally positioned, removable guide. On the surface of the conical head is a raised, spiral, knife edge for removing tissue samples. Extracted tissue samples are cut by the knife edge and retained inside the hollow conical head. As in the Spencer instrument, the head is disassembled for removal of collected tissue samples.

U.S. Pat. No. 4,243,048 to Griffin describes a biopsy instrument using a design different from those indicated above. The Griffin device has an annular cutting blade and slidably movable, cone-shaped anvil. Tissue samples are positioned between the annular blade and anvil. The anvil is then moved toward and against the cutting blade to sever tissue therebetween.

To be optimally effective, there are certain characteristics which should be present in an endocervical biopsy instrument. First, the instrument should be of unitary construction, having no movable or removable parts. Such parts could accidentally disengage from the instrument during sample extraction, causing internal damage to the patient. The instrument should also be capable of storing and retaining collected samples without permitting accidental spillage of the samples during removal from the patient. Moreover, the instrument should be designed to permit removal of samples from the instrument without time-consuming disassembly of the cutting head. Finally, the cutting head of the instrument should be designed to avoid the accidental combination of tissue from one sampling zone in the cervix with tissue from other regions of the cervix. For example, an instrument should be capable of extracting endocervical tissue samples without simultaneously extracting and combining tissues from other adjacent tissue regions. Since one part of the cervix may be cancerous and another part noncancerous, the mixture of tissues from both cervical regions could increase the likelihood of diagnostic error during sample analysis. Also, combining tissues from various regions of the cervix makes it increasingly difficult to determine which portions of the cervix are cancerous and which portions are not. These problems could ultimately result in unnecessary surgery and more extensive therapy.

Because none of the presently known endocervical biopsy instruments comprises a combination of the above-described features, a need presently exists for such an instrument.

SUMMARY OF THE INVENTION

An object of the present invention is to provide an endocervical biopsy instrument which is inexpensive to manufacture and use.

Another object of the present invention is to provide an endocervical biopsy instrument which is easily manipulated during tissue sample extraction.

A further object of the present invention is to provide an endocervical biopsy instrument which minimizes the risk of accidental injury to a patient during use.

A further object of the present invention is to provide an endocervical biopsy instrument which permits fast and easy tissue sample removal from the instrument after extraction.

A further object of the present invention is to provide an endocervical biopsy instrument which minimizes the likelihood of tissue sample spillage during extraction.

A further object of the present invention is to provide an endocervical biopsy instrument which permits sampling to occur with a high degree of accuracy.

A still further object of the present invention is to provide an endocervical biopsy instrument which avoids the accidental contamination of tissue taken from one sample zone with tissue from adjacent regions.

These and other objects, features, and advantages of this invention will be appreciated as the same becomes better understood by reference to the following detailed description and accompanying drawings.

DETAILED DESCRIPTION

Figure 1:
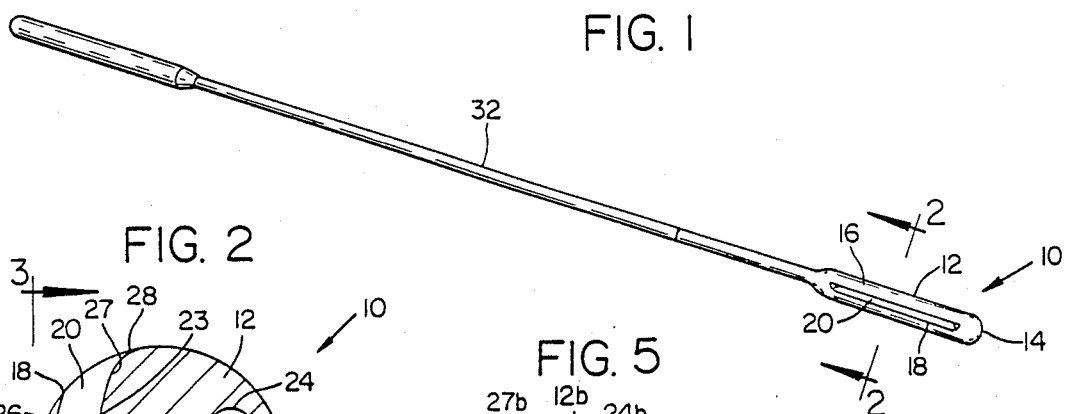
FIG. 1 is a perspective view of a preferred embodiment of the present invention.
Figure 2:
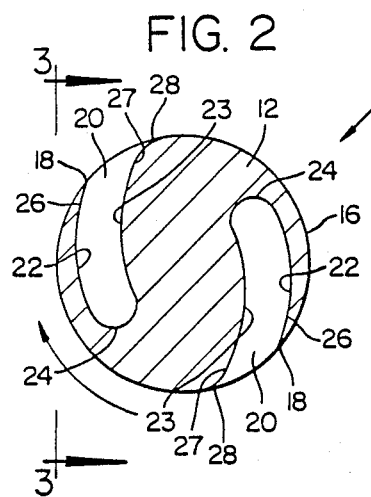
FIG. 2 is a cross sectional view of the embodiment of FIG. 1 taken along line 2—2 thereof.
Figure 3:
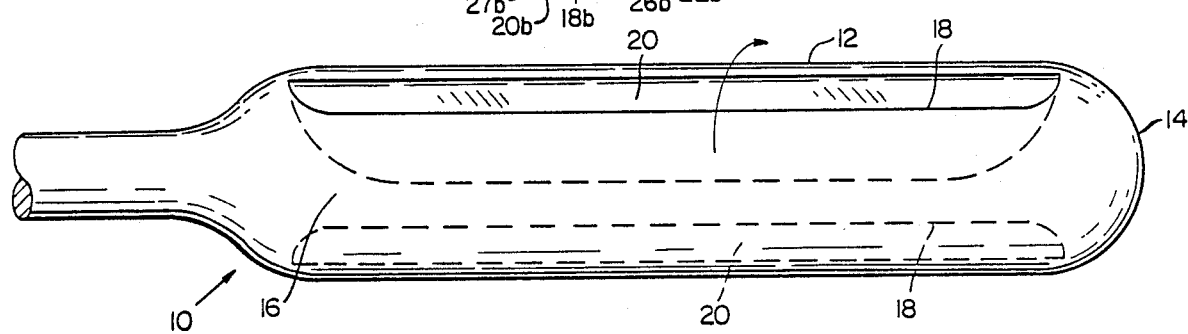
FIG. 3 is an enlarged side elevational view of the embodiment of FIGS. 1 and 2 taken along line 3—3 of FIG. 2.

FIGS. 1, 2 and 3 illustrate one embodiment of an instrument 10 according to the present invention. The instrument 10 is comprised of a cutting head 12 cylindrical in shape having a blunt, rounded tip 14. The head is of unitary design, "unitary" referring to the total absence of removable or detachable components. The head 12 is circular in cross section along its entire longitudinal axis. The length of the head 12 is of variable size, with a preferred range of between 10–40 millimeters. The diameter is also variable although a range of 3–7 millimeters is preferred.

With particular reference to FIGS. 2 and 3, coextensive with the surface 16 of the cutting head 12 are two longitudinal blades 18. The term "coextensive" refers to a structural relationship whereby the entire cutting edge of each blade 18 lies in and is integral with the surface 16 of the cutting head 12. In addition, each blade 18 is substantially parallel to the longitudinal axis of the cutting head 12.

Directly adjacent each blade 18 is a longitudinal sample-retaining well 20. It is desired that each well 20 be as deep as possible, and at least two thirds the diameter of the cutting head 12. This depth is sufficient to retain extracted tissue samples within the well 20 during a biopsy. As shown in FIG. 2, each well 20 is defined by walls 22, 23 and a bottom 24. Wall 23 is spaced inwardly from wall 22, and walls 22, 23 are also parallel to each other as is illustrated in FIG. 2. The upper portion 26 of each wall 22 terminates in a blade 18. The upper portion 27 of each wall 23 terminates in a rounded edge 28.

Each of the blades 18 and adjacent wells 20 in the present invention preferably extend the entire length of the cutting head 20, although both may be shortened as desired.

The cutting head 12 of the present invention may be permanently affixed to an elongate handle member 32 shown in FIG. 1, or disengageable therefrom. Disengagement may be accomplished by a thread arrangement (not shown) in which the head 12 is unscrewed from the handle member 32. It is preferred, as shown in FIG. 1, that the cutting head 12 be of greater diameter than the elongate handle member 32 in order to facilitate manipulation of the cutting head within the endocervical canal.

Figure 4:
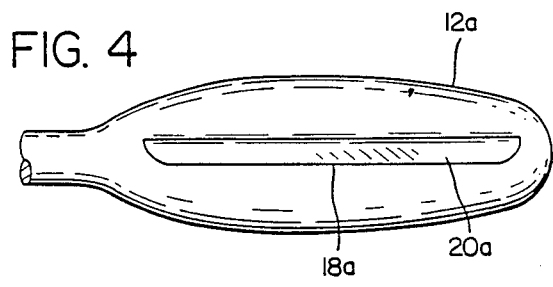
FIG. 4 is a side elevational view of another embodiment of the present invention having a longitudinally ellipsoid-shaped sample extraction head.

In addition to the embodiment of FIGS. 1, 2 and 3, other embodiments of the invention are shown in FIGS. 4–10. In these embodiments, the shape of the cutting head, the number of blades and wells, and the orientation of the blades and wells are varied. For example, FIG. 4 shows a cutting head 12a longitudinally ellipsoid in shape. As in all contemplated forms of the present invention, the head 12a is circular in cross section and of unitary construction. The blade 18a and well 20a of the cutting head shown in FIG. 4 are identical in construction to those shown in FIGS. 1, 2, and 3.

Figure 5:
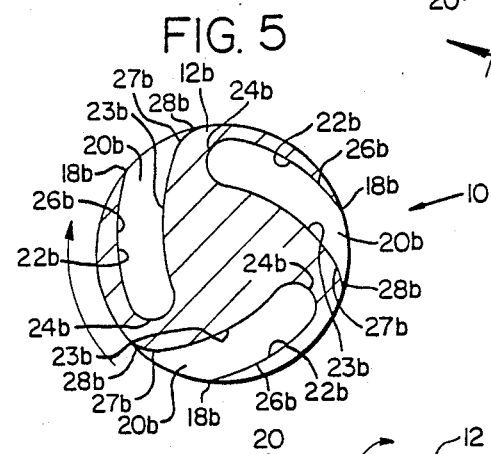
FIG. 5 is a cross sectional view of a still further embodiment of the present invention showing a sample extraction head having three blades and three sample-retaining wells.

FIG. 5 represents an embodiment in which the number of blades and wells on the head are varied. Specifically, FIG. 5 shows a cross section of a substantially cylindrical or ellipsoid head 12b in which three blades 18b and three wells 20b are disposed. The blades 18b and wells 20b are of the same design and configuration as those shown in FIG. 2. For example, each well 20b is defined by walls 22b, 23b and a bottom 24b. The upper portion 26b of each wall 22b is terminated by a blade 18b. The upper portion 27b of each wall 23b is terminated by a rounded edge 28b. It may be possible to further vary the number of blades and wells in the present invention, depending on the size of the cutting head.

Figure 6:
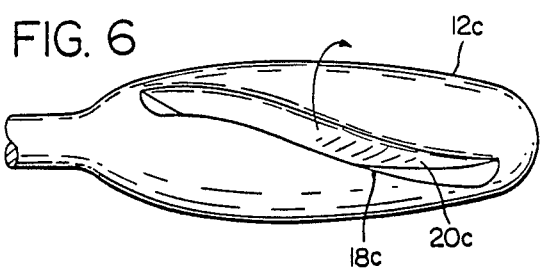
FIG. 6 is a side elevational view of a still further embodiment of the present invention wherein the sample extraction head has a blade and a sample-retaining well disposed in a helical orientation about the longitudinal axis of the head.
Figure 7:
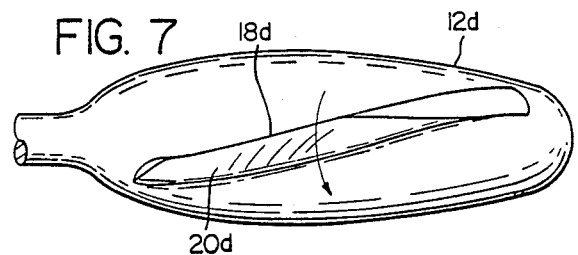
FIG. 7 is a side elevational view of a still further embodiment of the present invention wherein the sample extraction head has a blade and a sample-retaining well disposed in a helical orientation opposite that of FIG. 6.

The orientation of the blades and wells with respect to the longitudinal axis of the head may be varied. For example, FIG. 6 shows a head 12c having a blade 18c and well 20c in a helical orientation about the longitudinal axis of the cutting head 12c. FIG. 7 shows a head 12d with a blade 18d and well 20d in a helical orientation opposite that shown in FIG. 6. Other than the orientation of each blade and well in FIGS. 6 and 7, all other characteristics of the cutting head, blades, and wells are the same as those described above.

Each embodiment of the present invention discussed herein may be cast in metal well known in the art suitable for use in surgery. Each embodiment may also be detachable from an elongate handle member by means well known in the art. When metal construction materials are used, the cutting head can be sterilized and reused as often as desirable.

Figure 8:
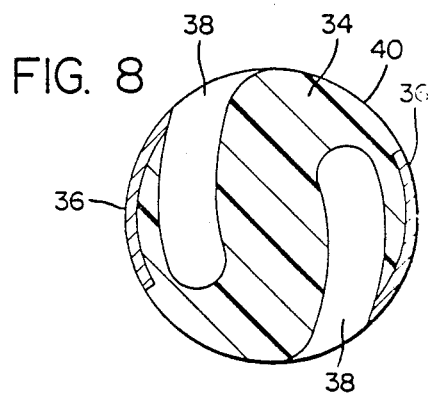
FIG. 8 is a cross sectional view of a still further embodiment of the present invention wherein the sample extraction head and blades are manufactured of different materials.

A disposable form of the present invention is shown in FIG. 8. This embodiment is essentially identical in design, structure, and function to the embodiment of FIGS. 1, 2, and 3. However, it consists of a head 34 made of a plastic material commonly used for surgical instruments. One or more blade members 36 are permanently attached to the head 34. The blade members 36 are attached during manufacture of the head 34. They are permanently bonded using appropriate adhesive materials. Adjacent to each blade 36 is a well 38 substantially the same as those shown in FIG. 2. The embodiment of FIG. 8 differs from the embodiment of FIGS. 1, 2, and 3 only in the materials used. For example, it is unitary in construction as defined herein, in that it contains no removable or detachable components. Also, the entire cutting edge of each blade 36 is coextensive with (i.e., lies in and is integral with) the arcuate surface 40 of the head 34. It is contemplated that the embodiment of FIG. 8 will be used only once, and then disposed of. This is economically feasible in view of the relatively low cost of plastic materials.

Figure 9:
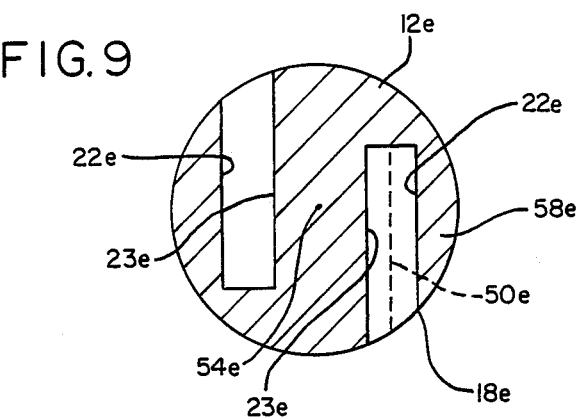
FIG. 9 is a cross sectional view of a still further embodiment of the present invention wherein the interior walls of the sample-retaining wells are straight in configuration.

FIG. 9 shows an embodiment of the present invention in which the side walls 22e and 23e are straight in configuration as opposed to the curved sidewalls shown in FIGS. 2 and 5. Such modification is principally designed to facilitate mass production of the invention by using conventional metal fabrication equipment. The basic functional characteristics of the invention remain the same.

Figure 10:
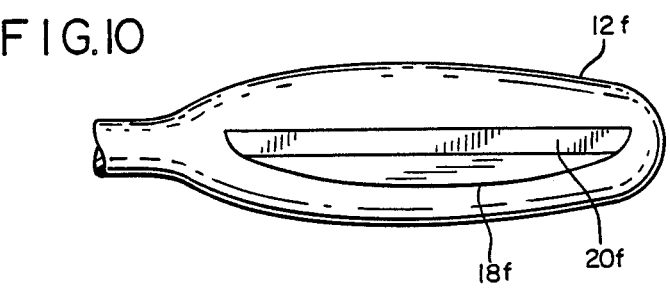
FIG. 10 is a side elevational view of a still further embodiment of the present invention wherein the blade portions of the sample extraction head have an arcuate configuration.

Finally, FIG. 10 discloses an embodiment of the present invention in which the blade portion 18f of the cutting head 12f adjacent the well 20f is arcuate in configuration. This design would be effective in various circumstances of use, depending on the condition of the patient and the individual preference of the surgeon.

The present invention represents a safe and efficient instrument for collecting tissue samples from the endocervical regions of a patient. The special configuration of the device, including the circular cross section of the cutting head, the longitudinal sample-retaining wells and the coextensive blades enhance the safety and efficacy of the device. More specifically, these benefits are achieved in all of the aforesaid embodiments using an arrangement in which each sample-retaining well includes at least two longitudinally extending interior walls, at least one of which is generally parallel to the exterior surface of the cutting head. As a result, the median plane between the two longitudinally extending interior walls is substantially offset from the centerline of the head. This arrangement, for example, is shown in FIG. 9, the median plane being designated in dashed lines using reference number 50e, with the centerline of the head 12e being designated at reference number 54e. Interior wall 22e is generally parallel to the exterior surface of the head 12e, as discussed above. The portion of the head 12e between the interior wall 22e and the exterior surface of the head 12e defines a region of the head 58e, which forms a longitudinal cutting blade with a sharp cutting edge 18e. These structural characteristics result in an improved surgical biopsy instrument which is capable of safely and efficiently extracting tissue samples from the endocervical canal.

Having described herein various embodiments of the present invention, it is not intended that the invention be limited to the specific forms described above. For example, the size of the cutting head, the number of blades and wells, the orientation of the blades and wells, and other parameters may be varied within the scope of the present invention. Thus, the present invention shall not be limited or restricted to specific details set forth herein, and the invention shall be considered as that falling within the scope of the following claims.

I claim:

1. A biopsy instrument for collecting tissue from the endocervical canal comprising a handle portion and a cutting head having a curved exterior surface, said head being circular in cross section and of a diameter greater than the diamater of said handle portion, said head comprising:

at least two sample retaining wells interiorly disposed within said head, each well being open at said surface of said head and being defined by a first and second interior wall, said second wall being closer to the center of said head than said first wall, said walls being parallel to each other;

each of said wells having a depth at least two-thirds the diameter of said head, whereby said depth enables samples to be retained and stored within said head during the rotational movements encountered in a biopsy procedure;

said first wall of each well comprising a sharpened edge portion terminating at the surface of said head, whereby said sharpened edge portion functions as a tissue cutting blade.

2. The biopsy instrument of claim 1 wherein said head is comprised of plastic and said sharpened edge portion is being comprised of metal, said sharpened edge portion permanently affixed to said head.

* * * * *

UNITED STATES PATENT AND TRADEMARK OFFICE
CERTIFICATE OF CORRECTION

PATENT NO. : 4,757,826
DATED : July 19, 1988
INVENTOR(S) : GAZI ABDULHAY

It is certified that error appears in the above-identified patent and that said Letters Patent is hereby corrected as shown below:

```
Column 6, line 19, "diamater" should be --diameter--
Column 6, line 38, delete "being".
Column 6, line 39, before "permanently" insert --being--.
```

Signed and Sealed this

Sixth Day of December, 1988

*Attest:*

DONALD J. QUIGG

*Attesting Officer*  *Commissioner of Patents and Trademarks*